United States Patent [19]

Goosen et al.

[11] Patent Number: 4,689,293
[45] Date of Patent: * Aug. 25, 1987

[54] MICROENCAPSULATION OF LIVING TISSUE AND CELLS

[75] Inventors: Mattheus F. A. Goosen; Geraldine M. O'Shea, both of Toronto; Anthony M. F. Sun, Willowdale, all of Canada

[73] Assignee: Connaught Laboratories Limited, West Willowdale, Canada

[*] Notice: The portion of the term of this patent subsequent to Jun. 16, 2004 has been disclaimed.

[21] Appl. No.: 677,985

[22] Filed: Dec. 4, 1984

Related U.S. Application Data

[63] Continuation of Ser. No. 501,445, Jun. 6, 1983, abandoned.

[51] Int. Cl.⁴ .............................................. A01N 1/02
[52] U.S. Cl. ....................................... 435/1; 424/110; 424/424; 435/178; 435/240.22; 604/891; 604/892; 604/896
[58] Field of Search ............... 424/21, 16, 110; 435/1, 435/178, 240, 241; 604/891, 892, 896

[56] References Cited

U.S. PATENT DOCUMENTS 4,352,883 10/1982 Lim ..................................... 435/178
4,353,888 10/1982 Sefton ................................... 424/16

OTHER PUBLICATIONS

O'Shea et al.–Biochem at Biophysic Acta vol. 804 (1984) pp. 133–136.
Lim et al.–Science vol. 210 (Nov. 1980) pp. 980–910.

*Primary Examiner*—Sam Rosen
*Attorney, Agent, or Firm*—Lahive & Cockfield

[57] ABSTRACT

Living tissue or cells, for example, islets of Langerhans, are microencapsulated for implantation in the body for long term treatment of diabetes or other disease requiring organ transplantation. The microcapsules take the form of a biocompatible semi-permeable hydrogel membrane which permits the passage of materials and oxygen to the cells and metabolic products from the cells while retaining the cells encapsulated. The biocompatible semi-permeable membrane has an outer negatively-charged surface, which imparts to the microcapsules the ability to maintain long term effectiveness.

18 Claims, No Drawings

MICROENCAPSULATION OF LIVING TISSUE AND CELLS

This is a continuation of application Ser. No. 501,445, filed June 6, 1983, now abandoned.

FIELD OF INVENTION

The present invention is concerned with the microencapsulation of living tissue or individual cells.

BACKGROUND TO THE INVENTION

Various attempts have been made to microencapsulate biologically active macromolecules, tissue and individual cells so that they remain viable and in a protected state within a semi-permeable membrane which permits passage of low molecular weight substances, such as nutrients and oxygen, but not of high molecular weight substances, such as, proteins and cells. However, none of these attempts has been successful in providing microcapsules in which tissue or cells enclosed within the semi-permeable membrane are able to survive in an animal body for longer than 2 to 3 weeks, which severely limits the utility of the products in the treatment of diseases requiring organ transplantation, such as diabetes.

In "Semipermeable Microcapsules" by T. M. S. Chang, Science, 146, 1964, 524 to 525, there is described the microencapsulation of erythrocyte hemolysate and urease in semi-permeable polyamide (nylon) membranes. These microcapsules did not survive for long when injected into the blood stream. Papers have described the preparation of semi-permeable microcapsules containing microbial cells and viable red blood cells, namely K. Mosbach and R. Mosbach, Acta Chem. Scand., 20, 1966, 2807 to 2812 and T. M. S. Chang, F. C. MacIntosh and S. G. Mason, "Semi-permeable Aqueous Microcapsules", Can. J. Physiol. and Pharmacology, 44, 1966, 115 to 128. The Chang et al article mentions for the first time the possibility of using injections of encapsulated cells for organ replacement therapy.

The next significant development was the use of calcium and aluminum alginate gels for the immobilization of microbial cells and enzymes. The cells were immobilized under extremely mild conditions, thus maintaining their viability. This work was described in V. Hackel, J. Klein, R. Megret and F. Wagner, Europ. J. Appl. Microbiol., 1, 1975, 291 to 296 and M. Kierstan and C. Bucke, "The Immobilization of Microbial Cells, Subcellular Organelles, and Enzymes in Calcium Alginate Gels", Biotechnology and Bioengineering, 19, 1977, 387 to 397.

Subsequently, viable tissue and cells were immobilized in alginate droplets coated with polylysine (F. Lim and R. D. Moss, "Microencapsulation of Living Cells and Tissues", J. Pharm. Sci. 70, 1981, 351 to 354). While the cells remained viable in culture for up to two months, no experiments are described to test the in-vivo biocompatibility of the polylysine membrane. At approximately the same time, there was reported for the first time, the use of microencapsulated islets to correct the diabetic state of diabetic animals, in F. Lim and A. M. Sun, "Microencapsulated Islets as Bioartificial Pancreas", Science, 210, 1980, 908 to 909. However, the microcapsules, consisting of an inner alginate core, followed by a polylysine coat and an outer polyethyleneimine membrane, were rejected by an animal body within 2 to 3 weeks of implantation due to the poor biocompatibility of the outer polyethyleneimine membrane.

Formation of the latter microcapsules also is described in U.S. Pat. No. 4,352,883 F. Lim. As set forth therein, finely divided living tissue is suspended in an aqueous medium which contains sodium alginate, the suspension is formed into droplets of a size to envelope tissue, the droplets are gelled by conversion to calcium alginate to form discrete, shape-retaining temporary capsules, a permanent semi-permeable membrane is formed about the temporary capsules, and the calcium alginate gel is reliquified within the membrane by ion exchange. Example 3 of the patent describes injection of the microcapsules into diabetic rats. Polyethyleneimine contains imino groups, which induce granuloma, resulting in an inflammatory response from the body, which, in turn, destroys the polymer. Polyethyleneimine, therefore, is not biocompatible and the microcapsules are ineffective for organ replacement therapy for a period lasting longer than 2 to 3 weeks.

U.S. Pat. No. 4,352,883 mentions the possibility of using polylysine, a much more biocompatible material, instead of polyethyleneimine as the membrane. Polylysine is positively charged and it is well known that positively-charged surfaces are excellent substrates for cell growth. Cell growth on the surface of the microcapsules, such as would occur with a polylysine membrane, would transform the semipermeable capsular wall to an impermeable one, resulting in the death of the encapsulated tissue.

It is apparent, therefore, that there is a need for the development of microcapsules which can be implanted into an animal body and be effective in the treatment of diseases requiring organ transplantation, such as, diabetes, for extended periods of time.

SUMMARY OF INVENTION

In accordance with the present invention, it has now surprisingly been found that living cells can be microencapsulated and the resulting microcapsules have long term in vivo activity by encapsulating the cells within a biocompatible semi-permeable membrane which has an outer surface of biocompatible negatively-charged material. The present invention, therefore, provides biocompatible microcapsules suitable for implantation in a mammalian body comprising encapsulated viable tissue or individual cells within a biocompatible semi-permeable membrane having a biocompatible negatively-charged surface. While the present invention has particular application to the microencapsulation of living cells, any desired macromolecular core material may be provided in the form of microcapsules, such as, enzymes, immunoproteins and activated carbon particles. The macromolecular core material is surrounded by a biocompatible semi-permeable membrane which is permeable to small molecules for contact with the core material but is impermeable to the core material, and also to potentially deleterious large molecules.

GENERAL DESCRIPTION OF INVENTION

In the present invention, core material, such as, living tissue, individual cells or biologically-active materials, are encapsulated in a biocompatible semi-permeable membrane, in the form of a hydrogel. The material to be encapsulated is suspended in a physiologically-compatible medium containing a water soluble substance which can be reversibly gelled to provide a temporary protective environment for the tissue. The medium is formed into droplets containing the tissue and gelled, for example, by changing conditions of temperature, pH or ionic environment, to form temporary capsules, preferably of substantially perfect spherical shape so as to provide an overall improved physical strength when compared with microcapsules formed from non-spherical capsules. Thereafter, the temporary capsules which result are treated to form a membrane of controlled permeability about the shape-retaining temporary capsules. The semi-permeable nature of the membrane permits nutrients and oxygen to flow to the core material and metabolic products to flow therefrom while retaining the core material within the microcapsule. The biocompatible nature of the semi-permeable membrane allows the passage of such materials to and from the core to occur without inflammation or other adverse body response while the outer negatively-charged surface inhibits surficial cell growth, so that the membrane remains semi-permeable and effective for extended periods of time, typically from three to six months or longer.

The temporary capsules may be formed from any non-toxic water-soluble substance that can be gelled to form a shape retaining mass by a change of conditions in the medium in which it is placed, and also comprises plural groups that are readily ionized to form anionic or cationic groups. The presence of such groups enables surface layers of the capsule to cross-link to produce a permanent membrane when exposed to polymers containing multiple functionalities of the opposite charge.

Preferably, the temporary capsules are formed from a polysaccharide gum, which may be natural or synthetic, of a type that can be gelled to form a shape retaining mass by exposure to a change in conditions and can be permanently cross-linked or hardened by polymers containing reactive groups, such as amino groups, which can react with the acidic polysaccharide constituents. Most preferably, the gum is alkali metal alginate, specifically sodium alginate, although other water-soluble gums may be used.

The temporary capsules may be formed from sodium alginate by extruding droplets of aqueous sodium alginate solution into an aqueous calcium chloride solution. As noted above, it is preferred that the temporary capsules be substantially spherical and it has been found that substantially perfectly spherical temporary capsules can be formed by using an aqueous sodium alginate solution having a viscosity of at least about 30 centipoise. At viscosities below this critical lower limit, the temporary capsules have an irregular shape. Perfectly spherical capsules are obtained over a wide range of viscosity of the sodium alginate solution, with an upper limit being dictated largely by the ability to extrude the solution into the hardening medium. Usually, the viscosity of the aqueous sodium alginate solution does not exceed about 1000 cps.

Formation of the permanent semi-permeable membrane about the temporary capsules preferably is effected by ionic reaction between free acid groups in the surface layer of the gelled gum and biocompatible polymers containing acid-reactive groups, such as, amino groups, typically in a dilute aqueous solution of the selected polymer.

Cross-linking biocompatible polymers which may be used include polylysine and other polyamino acids. It is noted that polyethyleneimine and other imine-containing polymers are unsuitable for membrane formation in view of the non-biocompatible nature. The molecular weight of the polyamino polymer may vary widely, depending on the degree of permeability required, and typically is in the range of about 11,000 to about 400,000, preferably about 11,000 to about 100,000. The use of polylysine or other polyamino acid results in microcapsules having a positively-charged surface, which, as already noted, would be unsuitable for long term viability, although the microcapsules are biocompatible.

In accordance with the presence invention, the semi-permeable membrane is treated with a non-toxic biocompatible water-soluble polymeric material which is capable of ionic reaction with free amino groups to form an outer negatively-charged coating about the membrane, typically by suspension of the microcapsules in an aqueous solution of the polymeric material. The material used to form the outer coating preferably is the same material as is used to form the temporary capsules, preferably a polysaccharide gum, more preferably an alkali metal alginate, such as, sodium alginate. Other biocompatible polymeric materials containing base-reactive groups, such as, polyvinyl alcohol, polylactic acid, poly glycolic-lactic acid copolymers and poly beta-hydroxy butyric acid, may be used to form the outer coating to the microcapsules. Molecular weights of such polymeric materials typically vary from about $10^4$ to about $10^6$.

The treatment of the polyamino microcapsules with the biocompatible base-reactive material retains the overall biocompatible nature of the semi-permeable membrane and, more importantly, results in a negatively-charged outer surface which inhibits cell growth and, therefore, permits the semi-permeable membrane to retain its permeability and hence effectiveness over an extended period of time.

Following formation of the microcapsules, reliquification of the suspending medium for the core material may be effected by re-establishing the conditions under which the material is liquid. This may be achieved by ion exchange to remove multivalent cation, for example, by immersion in phosphate buffered saline or citrate buffer.

The process of the invention may be used to encapsulate living tissue, multicellular fractions thereof or individual cells, for example, islets of Langerhans, liver cells and red blood cells, and other biologically-active material. The microcapsules which result may be implanted into a appropriate site within a mammalian body for the purpose of providing the body with the specialized physiological function of the tissue while the tissue remains viable. The implantation may be achieved by simple injection, so that surgical procedures are not required.

The biocompatible semi-permeable membrane encapsulating the core material consists of interpenetrating layers of ionically-interacted biocompatible materials. The overall wall thickness of the semi-permeable membrane usually varies from about 5 to about 20 $\mu$m. The microcapsules themselves usually have a diameter in the range of about 50 to about 2000 $\mu$m, preferably in the range of about 200 to about 1000 $\mu$m for microcapsules containing islets of Langerhans as the core material. The biocompatible semi-permeable membrane is in the form of a hydrogel and hence has an overall water content within the membrane structure of at least about 20 wt%, which may vary up to about 90 wt% in the surface region.

The materials which are used to form the biocompatible semi-permeable membrane are biodegradable by the body into which the microcapsules are implanted. Such biodegradation takes place over the active life of the microcapsules and is responsible for the ultimate failure of the microcapsules. The biodegradation is a very slow process, as is evidenced by observed effectiveness of the control of blood sugar in rats by microencapsulated islets of Langerhans of at least three months and, in some cases, as long as one year.

DESCRIPTION OF PREFERRED EMBODIMENT

In a particularly preferred embodiment of the invention, living cells are microencapsulated within a polylysine-alginate semi-permeable hydrogel by suspending cells uniformly in a sodium alginate solution in physiological saline. Where the microcapsules are to be used for the treatment of diabetes by controlling blood sugar in animals, including humans, the living cells take the form of islets of Langerhans from an animal pancreas.

Spherical droplets containing the cells are produced from an aqueous sodium alginate solution by a droplet generator, such as, syringe pump extrusion or electrostatic extrusion, and are collected as gelled spheres in a hardening solution, such as, calcium chloride. The microcapsules then are coated with polylysine followed by an outer coating of sodium alginate. The microcapsules may then be suspended in isotonic sodium citrate or other convenient ion exchange medium to reliquify the alginate gel inside the microcapsule.

The outer biochemically inert but biocompatible alginate surface is a negatively-charged hydrogel containing up to about 90% water. The low interfacial tension between the swollen gel surface and the aqueous biological environment minimizes protein interaction, otherwise a strong protein-polymer interaction may cause a severe inflammatory response. The biocompatibility of the hydrogel membrane leads to long term viability of the capsules when implanted. Polyethyleneimine-surfaced microcapsules do not appear to possess this property and hence are rejected by the body and produce a strong inflammatory response, which severely limits the useful life of the microcapsules within the body. The soft rubbery consistency of most hydrogels may also contribute to their biocompatibility by decreasing frictional irritation to surrounding tissues.

The durability of the microcapsules can be increased further by increasing the thickness of the polylysine membrane, as compared with the thickness of the polylysine-polyethyleneimine membrane used in U.S. Pat. No. 4,352,883. The strength of the microcapsules also may be increased by cross-linking, for example, using glutaraldehyde, prior to reliquification of the gel.

In the present invention, it is not essential that the biocompatible outer surface be composed of sodium alginate, but it is essential that the outer surface be biocompatible and negatively-charged. Binding occurs between the negatively-charged groups, usually hydroxyl or carboxyl groups, and the positively-charged amino groups on polylysine.

The permeability of the microcapsule to nutrients and metabolic products may be varied by varying the molecular weight of the polylysine used in forming the semi-permeable membrane. Usually, the molecular weight of the polylysine varies from about 11,000 up to about 400,000, preferably about 11,000 to about 100,000. Higher molecular weights lead to greater permeability than lower molecular weights.

EXAMPLES

Example 1

This Example illustrates the microencapsulation of islets of Langerhans.

Cultured rat islets of Langerhans ($2 \times 10^3$ islets in 0.2 ml medium) were suspended uniformly in 2 ml of a 1.5% (w/w) sodium alginate solution (viscosity 51 cps) in physiological saline. Spherical droplets containing islets were produced by syringe pump extrusion through a 22-gauge needle and collected in 1.5% (w/w) calcium chloride solution. The supernatant was decanted and the gelled spherical alginate droplets, containing islets, were washed with dilute CHES (2-cyclohexylamino-ethane sulfonic acid) solution and 1.1% calcium chloride solution.

After aspirating off the supernatant, the gelled droplets were incubated for exactly 6 minutes in 0.05% (w/w) polylysine having a molecular weight of 25,000. (These conditions are a significant increase in incubation time and polylysine concentration compared to the procedures in U.S. Pat. No. 4,352,883, wherein Lim used 0.013% polylysine and 3 minutes incubation time, and in the reported work of Lim and Sun where they used 0.02% polylysine and 3-5 minutes incubation time. These changes result in a stronger polylysine membrane.)

The supernatant was decanted and the polylysine capsules were washed with dilute CHES, 1.1% calcium chloride solution and physiological saline. The washed polylysine capsules were incubated for 4 minutes in 30 ml of 0.03% sodium alginate to permit the formation of an outer alginate membrane on the initial polylysine membrane, by ionic interaction between the negatively charged alginate and the positively charged polylysine.

The resulting microcapsules were washed with saline, 0.05M citrate buffer for 6 minutes to reliquify the inner calcium alginate, and a final saline wash. The microcapsules were found to be perfectly spherical and each to contain from 1 to 2 viable islets. The microcapsules had diameters varying from 200 to 1000 μm and wall thicknesses varying from 5 to 10 μm. The microcapsules were suspended in nutrient medium at 37° C.

The experiment was repeated with islet cells from mouse, bovine and dog pancreas and similar microencapsulated products were formed.

Example 2

This Example illustrates the viability of the microencapsulated islets.

In perifusion experiments, the insulin secretion from the microencapsulated rat islets produced in accordance with the procedure of Example 1 was determined to be comparable with that from unencapsulated islets. When the glucose concentration was raised from 50 to 300 mg, there was a biphasic response of insulin release from both groups of islets and the insulin secretion increased.

The increase in the quantity of insulin in the presence of a high glucose concentration clearly demonstrated that the viability and functionality of the cells were retained throughout the process of microencapsulation.

After 2 months in culture at 37° C., the microencapsulated islets were observed to have remained morphologically and functionally intact.

Example 3

This Example illustrates the injection of microencapsulated islets into diabetic rats.

Diabetic rats with blood glucose levels in the range of 370 to 470 mg/dL were treated with approximately $3 \times 10^3$ rat islets microencapsulated as set forth in Example 1. The microcapsules were introduced by injection into the peritoneal cavity using a 16-gauge needle fitted into a syringe.

Unencapsulated islets and islets microencapsulated in a polylysine-polyethyleneimine membrane, produced as described in U.S. Pat. No. 4,352,883 (Lim), were used as controls. Blood glucose levels were assayed twice per week to determine the period of time for which the blood glucose level was lowered. The results obtained are set forth in the following Table I:

TABLE I

| Membrane Type | Number of Weeks Blood Glucose Level Lowered | |
|---|---|---|
| None | 1 | (N = 4) |
| Polylysine polyethyleneimine (Lim Patent) | 2 to 3 | (N = 8) |
| Polylysine alginate (Present invention) | 13 to 52 | (N = 10) |

As can be seen from the results of Table I, the islets enclosed in the biocompatible polylysine alginate membranes of the invention survived up to 52 weeks, as demonstrated by the normal blood sugar levels in the diabetic rats. In contrast, the islets enclosed in the polylysine-polyethyleneimine capsular membranes of the Lim Patent showed survival times of less than 3 weeks.

Example 4

This Example shows the effect of multiple injections of microencapsulated islets.

The procedure of Example 3 was repeated except that, following a return to hyperglycemia (blood sugar concentration greater than 300 mg/dL), a second injection of polylysine alginate microencapsulated islets produced in accordance with the procedure of Example 1 normalized the blood sugar level of the animal for a longer period than the initial injections, allowing the blood sugar level of the diabetic rats to be controlled for longer than six months with just two injections.

In contrast, five injections of polylysinepolyethyleneimine microencapsulated islets at 2 to 3 week intervals were barely able to control the blood glucose level of diabetic animals for three months (N=8).

Example 5

This Example illustrates the injection of microencapsulated rat islets into diabetic mice.

The procedure of Example 3 was repeated except that fewer islets were used (1000 rat islets) and diabetic mice were employed. No polylysine polyethyleneimine microcapsules were used as controls.

Blood sugar levels in the diabetic mice were controlled for more than two months with a single injection (I.P.), indicating that xenograft transplants (cross-species) are possible.

Example 6

This Example illustrates the viability of recovered microencapsulated transplanted islets.

Microencapsulated islets were recovered from some of the treated diabetic rats in Example 3 at 3, 5 and 12 months postimplantation. The majority of the microcapsules were still physically intact and contained viable insulin-secreting islets, as demonstrated by secretion of insulin from the recovered islets in culture in response to a high glucose concentration.

Example 7

This Example illustrates the microencapsulation of liver cells.

The procedure of Example 1 was repeated, except that liver cells were employed in place of islets. An electrostatic droplet generator was employed in place of the syringe pump extruder to produce smaller capsules of diameter from 100 to 300 $\mu$m. Capsules containing viable liver cells were obtained, as determined by trypan blue exclusion and a histological study. Each capsule was observed to contain about 300 liver cells.

Example 8

This Example illustrates the use of polyvinyl alcohol as the external surface of the microcapsules.

The procedure of Example 1 was repeated, except that 1.0% (w/w) solution of polyvinyl alcohol in phosphate buffered saline was used in place of the sodium alginate solution for formation of the outer membrane coating. The polyvinyl alcohol did not significantly alter the permeability of the capsular membrane.

Polyvinyl alcohol is known to be a biocompatible water-soluble polymer and has been used in many surgical applications, such as, thromboresistant coatings for artificial blood vessels, and hence the microcapsules produced in this Example are expected to exhibit similar blood sugar decreasing capability in diabetic animals to the microcapsules produced by the procedure of Example 1.

Example 9

This Example illustrates the use of polylactic acid as the external surface of the microcapsules.

The procedure of Example 1 was repeated, except that 0.1% (w/w) solution of polylactic acid in buffered saline was used in place of the sodium alginate solution for formation of the outer membrane coating. The polylactic acid was initially dissolved in dilute sodium hydroxide and then neutralized with hydrochloric acid. The ongoing viability of the islets in the microcapsules so produced was demonstrated with trypan blue staining. Polylactic acid is a biocompatible polymer that is currently in clinical use as suture material. It is expected, therefore, that the microcapsules produced in this Example will exhibit similar blood sugar decreasing capability in diabetic animals to the microcapsules produced by the procedure of Example 1.

Example 10

This Example illustrates the preparation of spherical calcium alginate droplets.

Sodium alginate solutions of varying concentrations (and hence viscosities) were extruded with a syringe pump through a 22 gauge needle into a 1.5% (w/w) calcium chloride hardening solution and the resulting gel droplets were collected and their physical shape observed. The results are reproduced in the following Table II:

TABLE II

| Sodium Alginate % (w/w) | Viscosity (cps) | Fractions of Droplets which are Spherical (%) |
| --- | --- | --- |
| 1.5 | 51 | 100 |
| 1.4 | 43 | 100 |
| 1.3 | 36 | 100 |
| 1.2 | 30 | 100 |
| 1.1 | 25 | <25 |
| 1.0 | 20 | 0 |
| 0.9 | 16 | 0 |
| 0.7 | 11 | 0 |
| 0.3 | 4 | 0 |

While in all instances, the droplets could be broadly described as "spheroidal", it will be apparent from Table I that it is only at concentrations of sodium alginate solution of 1.2% w/w and above, i.e. viscosities of 30 cps and above, that perfect spheres are formed.

Example 11

This Example illustrates variation of the microcapsule permeability.

The procedures of Examples 1, 8 and 9 were repeated, except that the molecular weight of the polylysine was varied, with microcapsules being produced from polylysine of molecular weight from 11,000 up to 400,000. The permeability of the resulting microcapsules was determined by the diffusion of serum albumin or $^{125}$I.Ig G (antibody) into and out of the microcapsules.

It was found that the use of the 400,000 molecular weight polylysine increased the permeability of the microcapsules while the use of the 11,000 molecular weight polylysine decreased the permeability of the microcapsules.

Capsules prepared using 0.075 wt% of mixed molecular weight polylysine in the process of Example 1, comprising 10 mg polylysine of 25,000 molecular weight and 5 mg of polylysine of 4,000 molecular weight were found to be less permeable to lysed red blood cells, when compared to capsules prepared with 0.075 wt% of polylysine of 25,000 molecular weight.

It was further found that the microcapsules having a polylactic acid outer coating had a greater permeability than the alginate and polyvinyl alcohol coated microcapsules at the same polylysine molecular weight.

The procedure of Example 1 was again repeated, except that the concentration of polylysine was doubled to 0.1% w/w and the contact time was doubled to 12 minutes, thereby increasing the thickness of the polylysine layer from about 5 μm to about 20 μm. The resulting microcapsules exhibit decreased permeability when compared to those produced in Example 1.

Example 12

This Example illustrates increasing the strength of the microcapsules.

The procedures of Examples 1, 8 and 9 were repeated, except that the microcapsules were placed in contact with 0.01% w/w glutaraldehyde for less than 60 seconds, just after the polylysine coating step or just before the citrate washing step. The microcapsules which result are more difficult to break physically (using fine tweezers) and also are more difficult to dissociate in a heparin solution, when compared with un-cross-linked material.

SUMMARY OF DISCLOSURE

In summary of this disclosure, the present invention provides novel microcapsules of living tissue or cells which have long term biocompatability and viability, and hence utility, in the treatment of diseases requiring organ transplantation, such as, diabetes. Modifications are possible within the scope of the invention.

What we claim is:

1. A biocompatible microcapsule, suitable for implantation into an animal body and having a diameter of about 50 to about 2000 μm, comprising:
   a macromolecular spherical core containing living tissue or individual cells thereof, said core being surrounded by a biocompatible semi-permeable membrane, said membrane consisting of interpenetrating layers of ionically interacted polylysine and alginate defining a membrane thickness of about 5 to about 20 μm, said biocompatible semi-permeable membrane being in the form of a hydrogel having an overall water content within the membrane structure of at least about 20 wt. %, the exterior of said membrane having an outer biocompatible negatively charged surface,
   said biocompatible semi-permeable membrane being permeable to and permitting nutrients and oxygen to flow from a body in which the microcapsule is implanted to said living tissue or individual cells thereof and permitting metabolic products of said living tissue to flow therefrom to the body in which the microcapsule is implanted and being impermeable to said living tissue to retain the living tissue within the microcapsule, said microcapsule being capable of resisting degradation and remaining permeable in vivo for at least two months.

2. The microcapsules of claim 1 wherein said living tissue is an animal tissue selected from the group consisting of islets of Langerhans, liver and individual cells thereof.

3. The microcapsule of claim 1 wherein the outer surface is comprised of alginate, polyvinyl alcohol or polylactic acid.

4. The microcapsule of claim 1 wherein said living tissue is islets of Langerhans or a fraction thereof whereby insulin flows from the microcapsules, and said biocompatible semi-permeable membrane remains effective for a period of at least three months on implantation of said microcapsule to control blood suger levels in the body in which the microcapsule is implanted.

5. The microcapsule of claim 4, wherein said islets of Langerhans are suspended in an aqueous medium.

6. A method of encapsulating a core material within a semi-permeable membrane which is a hydrogel having an overall water content within the membrane structure of at least about 20 wt. %, which method comprises:
   a. placing the material in an aqueous solution of a water soluble polymeric substance that can be reversibly gelled and which has free acid groups,
   b. forming the solution into droplets,
   c. gelling the droplets to produce discreet shape-retaining temporary capsules,
   d. forming biocompatible semi-permeable membranes about the temporary capsules by contact for at least 6 minutes between the temporary capsules and a polylysine polymer containing free amino groups to cause ionic reaction with the acid groups and the surface layer of the capsule, and e. contacting said microcapsules formed in step d with a biocompatible polymeric material which contains free negatively charged groups capable of ionic reaction with the free amino groups in a surface layer of the microcapsule, thereby forming an outer coating of said biocompatible polymeric material on said microcapsules, said semi-permeable membrane formation and said contact thereof with biocompatible polymeric material being such as to form microcapsules having a diameter of about 50 to about 2,000 um and a semi-permeable membrane thickness of about 5 to about 20 um, and being such as to produce microcapsules capable of resisting degradation and remaining permeable in vivo for at least two months.

7. The method of claim 6 wherein said core material comprises living tissue which is in finely-divided suspended form in said aqueous solution in step (a).

8. The method of claim 7 wherein said living tissue comprises islets of Langerhans whereby said microcapsules may be used to control blood sugar levels in diabetic animal bodies into which the microcapsules are implanted.

9. The method of claim 6 wherein said reversibly-gellable water-soluble substance is a polysaccharide gum.

10. The method of claim 9 wherein said gum is an alkali metal alginate.

11. The method of claim 6 wherein said polymer-containing free amino groups has a molecular weight of about 11,000 to about 400,000 daltons.

12. The method of claim 11 wherein said polylysine has a molecular weight of about 11,000 to about 100,000.

13. The method of claim 6 wherein said biocompatible polymeric material comprises a polysaccharide gum containing free acid groups.

14. The method of claim 6 wherein said biocompatible negatively-charged polymeric material is selected from the group consisting of polyvinyl alcohols having free hydroxyl groups and polylactic acids containing free acid groups.

15. The method of claim 6 wherein said reversibly-gellable water-soluble substance comprises sodium alginate, and said biocompatible polymeric material comprises sodium alginate.

16. The method of claim 10 wherein said alkali metal alginate is sodium alginate and the viscosity of said aqueous solution of sodium alginate is at least sufficient to result in the formation of substantially spherical temporary capsules.

17. The method of claim 16 wherein said aqueous sodium alginate solution has a viscosity of at least about 30 cps.

18. The method of claim 6 including the further step of reliquifying the gel within the semi-permeable membrane.

* * * * *